United States Patent
Buess et al.

[11] Patent Number: 6,083,755
[45] Date of Patent: Jul. 4, 2000

[54] METHOD FOR DETERMINING THE CLEANING ACTION ON A CLEANED OBJECT

[75] Inventors: Gerhard Buess, Tübingen; Peter Heeg, Ammerbuch; Klaus Roth, Ofterdingen; Jens-Peter Sieber, Calw-Altburg; Hartwig Schrimm, Leonberg; Rudolf Reichl, Metzingen, all of Germany

[73] Assignees: Eberhard-Karls-Universität; Tübingen Universitätsklinikum, both of Tübingen, Germany

[21] Appl. No.: 08/907,277

[22] Filed: Aug. 6, 1997

[30] Foreign Application Priority Data

Aug. 6, 1996 [DE] Germany .............. 196 31 668

[51] Int. Cl.[7] ................................. G01N 23/083
[52] U.S. Cl. .............. 436/55; 436/56; 73/60.11; 134/1
[58] Field of Search .................. 134/42, 1, 1.3; 436/55.56; 73/60.11, 60.41

[56] References Cited

U.S. PATENT DOCUMENTS

| | | | |
|---|---|---|---|
| 3,242,338 | 3/1966 | Danforth et al. | 250/106 |
| 3,546,464 | 12/1970 | Glass | 250/106 |
| 3,721,629 | 3/1973 | Goodenough | 134/3 |
| 4,651,000 | 3/1987 | Kravetz et al. | 73/60.11 |
| 5,494,530 | 2/1996 | Graf | 134/18 |

FOREIGN PATENT DOCUMENTS 63-315953 12/1988 Japan .............. G01N 33/543

OTHER PUBLICATIONS

Schrimm H., et al., "A New Method For Validating and Verifying the Cleaning of Tubular Instruments", *Zentr Steril,* vol. 2 (1994) pp. 313–324.

Mostafa, A.B. and Chackett, K.F., "Radioactive Tracers in the Assesment of Cleaning of Surgical Appliances", *International Journal of Applied Radiation and Isotopes,* vol. 26, (1975) pp. 651–655.

*Primary Examiner*—Lyle A. Alexander
*Attorney, Agent, or Firm*—Claude A. S. Hamrick; Oppenheimer W. Donnelly

[57] ABSTRACT

A method for determining cleaning action on medical instruments and other objects is disclose. The method uses a predetermined soiling substance, for example fresh blood mixed with a radioactive marker. The soiling substance is applied to the instrument as a predetermined contamination. By making various radiation and time measurements one can determine in absolute mass units either the remaining soiling after the completion of a cleaning process or the soiling prior to the cleaning process. By comparing the determined masses one may validate specific cleaning processes, machines or agents.

13 Claims, 2 Drawing Sheets

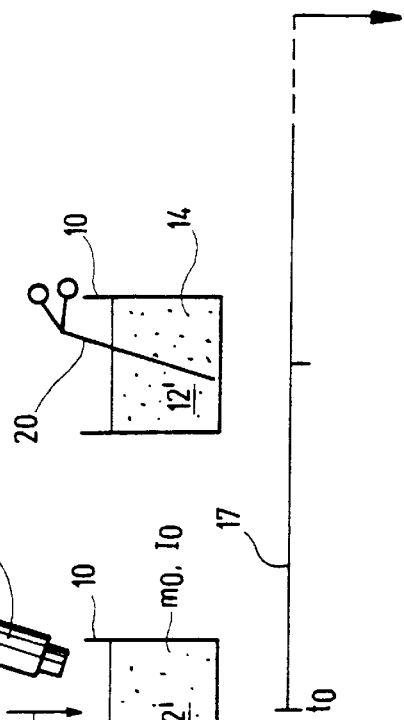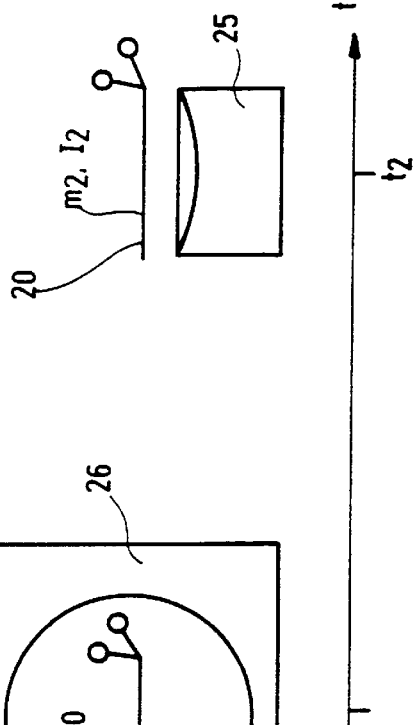

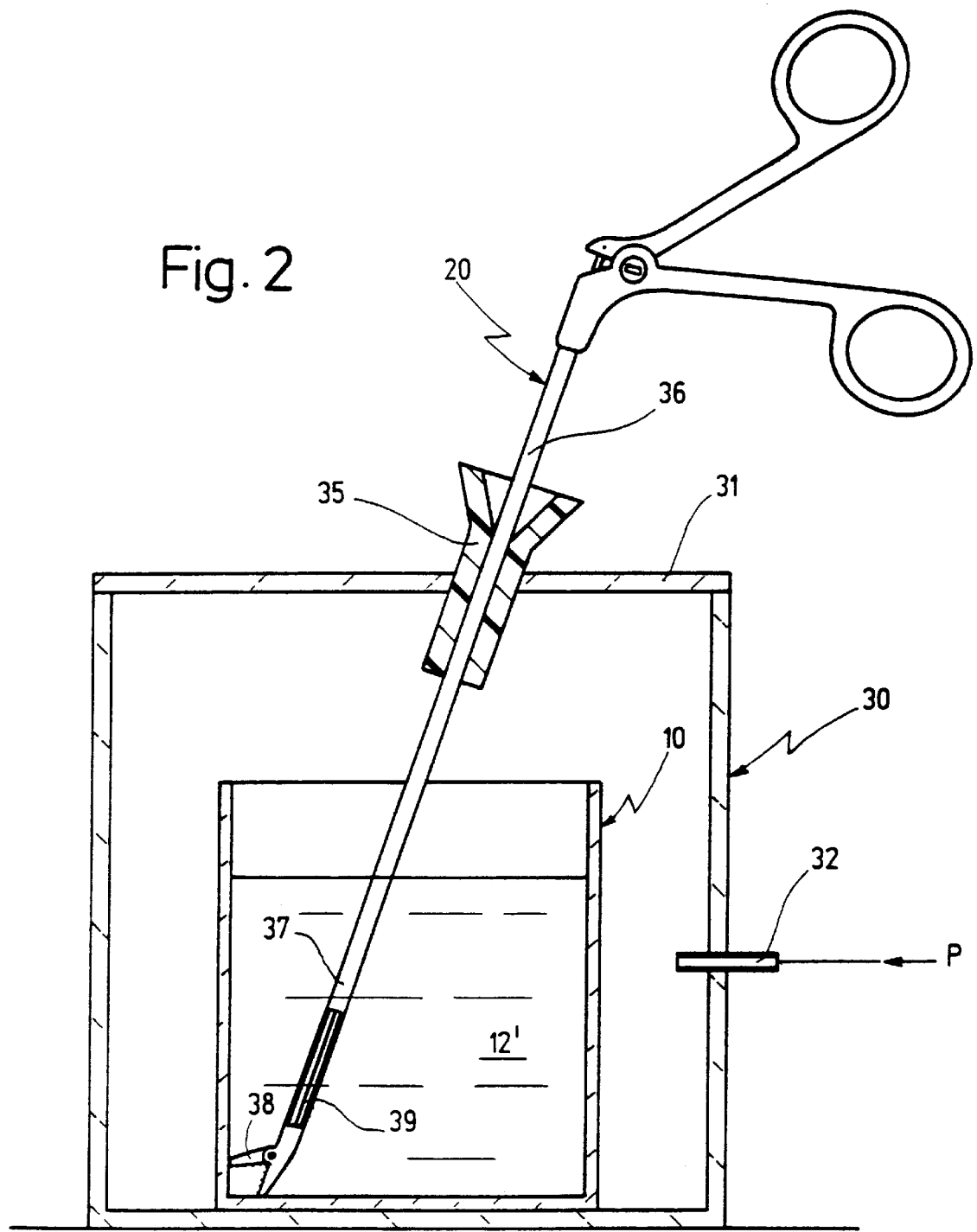

METHOD FOR DETERMINING THE CLEANING ACTION ON A CLEANED OBJECT

FIELD OF THE INVENTION

The present invention relates to a method for determining the cleaning action on a cleaned object.

The invention, further, relates to a method for determining the amount of soiling on objects to be cleaned.

The invention, further, relates to a method for optimizing the design-based cleanability of a medical instrument through determining the cleaning action on the instrument after having undergone a predetermined cleaning process.

The invention, further relates to a method for optimizing the cleaning of a washing machine through determining the cleaning action of the washing machine on an object cleaned by the washing machine.

The invention, further, relates to a method for optimizing the cleaning action of a cleaning agent through determining the cleaning action of the agent on an object cleaned by the agent.

The invention, further, relates to a method for validating a cleaning process through determining the cleaning action of the process on an object cleaned by the process.

The invention, further, relates to a method for optimizing the design-based cleanability of a medical instrument through determining the amount of soiling on the instrument before undergoing a predetermined cleaning process.

The invention, further, relates to a method for optimizing the cleaning action of a washing machine through determining the amount of soiling on an object to be cleaned by the washing machine.

The invention, further, relates to a method for optimizing the cleaning action of a cleaning agent through determining the amount of soiling on an object to be cleaned by the agent.

Finally, the invention relates to a method for validating a cleaning process through determining the amount of soiling on an object to be cleaned by the process.

BACKGROUND OF THE INVENTION

It is well-known that during the cleaning of medical instruments or of parts of food-treating machines or of parts of pharmaceutical installations it is highly mandatory that the cleaning action be as effective and complete as possible. For, it must be ensured under any circumstances that during the subsequent use of such objects a transfer of pathogenic agents, organisms, germs or viruses is absolutely excluded.

In the clinical area the protection against pathogenic agents or organisms is not achieved through the cleaning before the application of such instruments but instead through sterilization following the cleaning process. The object of the cleaning is to reduce the initial contamination of the instruments to be sterilized in order to increase the sterilization performance, the so-called sterilization probability. A further object of the cleaning process is to remove unwanted substances, i.e. to remove soiling in order to optimize the access of the sterilizing agents to those surfaces of the instruments that shall be treated.

Insofar, substantial problems arise in connection with the cleaning of so-called hollow shaft instruments as are used in the minimum invasive or endoscopic surgery. Such instruments are provided with an elongate tubular shaft. The tubular shaft has an operating element on its front terminal end, for example a medical forceps, whereas the rearward terminal end is provided with corresponding actuators, for example actuating levers. In order to interconnect the operating elements with the corresponding actuators, an appropriate rod or a Bowden pull wire is arranged within the hollow shaft.

During the application of such medical instruments the hollow shaft is, for example, pushed through the abdominal wall of a patient so that a surgical operation may be carried out on an inner organ of the patient by means of the operating elements. The operating elements as well as the lower portion of the hollow shaft will come in contact with blood or other body liquids. Due to a capillary action within the hollow shaft, these liquids will rise upwardly within the hollow shaft.

After the operation is finished, the instruments are normally not immediately cleaned because in ordinary hospitals the cleaning installations are normally located distant from the operating catheters. Due to the time lapsing accordingly, the liquid will partially dry on the instrument. The subsequent cleaning of the instrument may then be difficult for various reasons. First, the liquid may have penetrated into cavities, annular grooves and the like which are hardly accessible. Further, the liquid may have partially dried up for the reasons mentioned before so that the cleaning is also much for difficult for these reasons.

On the other hand side, instruments of the aforementioned kind are relatively expensive. Therefore, they have to be re-used as many times as possible. The same holds true for other invasive instruments, for example for rigid or flexible endoscopes. The same applies for other types of instruments which in spite of their relatively high price are until today used as disposables, for example catheters.

Similar problems arise in other areas, for example in the food industry or in the pharmaceutical industry where care must be taken that the parts of the machines treating food or pharmaceutical products have to be diligently cleaned after each working cycle.

For the reasons explained above, it is well-known that cleaning aspects have to be taken into account already during the design of the corresponding object, for example during the design of a medical instrument for endoscopic surgery. It is, therefore, well-known to optimize the design of such instruments under the aspect of cleanability. It is, for example, known to provide instruments of this kind with particular features, for example with rinsing channels or the like to facilitate cleaning after the use of such instruments.

On the other hand side, there is a need in the field of cleaning installations (washing machines) and of cleaning agents, respectively, for such objects, instruments etc. to continuously improve such products so that the difficult cleaning problems mentioned above and other comparable cleaning problems may be solved.

In view of this background there is a need to have a method enabling to determine the cleaning action under objective standards and reproducibly. If such a method were at hand, it would be possible to continuously refine the design of such objects and instruments by continuously applying the method. The same would apply for the design of cleaning installations and washing machines and also for the creation of cleaning agents because the cleaning action of such installations or agents could also be controlled with a reproducible method mentioned above. For optimizing the design of objects and instruments under cleanability aspects, the method would have to be applied on differently designed objects and instruments while using the same cleaning method, the same cleaning instruments and the same cleaning action for obtaining reproducible results during the evolution, i.e. optimization of the instrument or object design. In the case of the optimizing of cleaning installations, washing machines or cleaning agents, the method would have to be used on the same reference instruments or reference objects for varifying the cleaning action on a neutral and reproducible basis.

A method for validating and controlling the cleaning of hollow shaft instruments is disclosed in German journal "Zentral Sterilisation", 2 (1994), pp. 313–324.

According to this prior art method hollow shaft instruments are soiled with radioactively marked blood. The distribution of the test contamination so generated is topographically determined before and after the cleaning. For that purpose an experimental set up is used in used in which hollow shaft instruments are soiled with blood, where the blood had been provided with radioactive $99^{th}$ technetium. For that purpose makroalbumines are first provided with the radioactive technetium. The radioactive makroalbumines are then mixed with fresh, i.e. coagulable blood. By means of a γ-camera the soiled hollow shaft instruments are measured, are then rinsed and are finally measured a second time. The measurements are made by detecting the counts per second. The cleaning action is then determined through the ratio of the measured values before and after the cleaning. The natural half lifetime of technetium (approximately six hours) is taken into account.

This prior art method yields only relative results but no absolute results in view of the actual amount or mass of the remaining soiling. It is impossible to directly convert the measured counts per time into mass units because the behaviour of radioactively marked makroalbumines is not known in detail, in particular not in connection with the metallic environment. Further, the dissociative behavior of technetium in this regard is not known in detail. Due to these reasons the measurement may be faulty when in spite of the presence of a relatively large mass or residual soiling, only relatively small radiation (counts per time) is measured.

It is, therefore, an object underlying the invention to improve the methods of the kind as specified at the outset such that reproducible results are obtained, allowing in particular to actually determine the existing mass of residual soiling or any soiling quantitatively and, moreover, independent of the prevailing initial radiation at the moment when the inventive method is initiated.

According to a first group of inventive method in which the cleaning action on a cleaned object is determined, this object is met by the following method steps:

a) providing a predetermined soiling substance;
b) adding to said soiling substance a radioactive marker having a half life period T, said soiling substance provided with said radioactive marker having together a first mass $m_0$ and a radiation;
c) measuring said first mass $m_0$;
d) simultaneously with said measuring of said first mass $m_0$ measuring a first intensity $I_0$ of said radiation and starting a measurement of time t;
e) at least partially inserting said object into said soiling substance provided with said radioactive marker such that a second mass $m_1$ of said soiling substance provided with said radioactive marker is introduced into at least a portion of said object, thereby contaminating said object;
f) cleaning said object;

g) measuring a third intensity $I_2$ of said radiation at a moment in time $t_2$;
h) determining a third mass $m_2$ of a soiling having remained on said object after said step of cleaning according to the formula:

$$m_2 = \frac{I_2}{I_0} r_{(t,\ldots)} m_0 e^{(t_2/T)\ln 2}$$

where $r_{(t,\ldots)}$ is a predetermined proportionality function for taking into account the dissociative behaviour of bonding between the radioactive marker and the object as a carrier.

According to a second group of inventive methods in which the amount of soiling on objects is determined, the above-mentioned object is met by the following method steps:

a) providing a predetermined soiling substance;
b) adding to said soiling substance a radioactive marker having a half life period T, said soiling substance provided with said radioactive marker having together a first mass $m_0$ and a radiation;
c) measuring said first mass $m_0$;
d) simultaneously with said measuring of said first mass $m_0$ measuring a first intensity $I_0$ of said radiation and starting a measurement of time t;
e) at least partially inserting said object into said soiling substance provided with said radioactive marker such that a second mass $m_1$ of said soiling substance provided with said radioactive marker is introduced into at least a portion of said object thereby contaminating said object, said second mass $m_1$ having a radiation of a second intensity $I_1$;
f) measuring said second intensity $I_1$ of said second mass $m_1$ on said contaminated object at a moment in time $t_1$; and
g) determining said second mass $m_1$ according to the formula:

$$m_1 = \frac{I_2}{I_0} r_{(t,\ldots)} m_0 e^{(t_1/T)\ln 2}$$

where $r_{(t,\ldots)}$ is a predetermined proportionality function for taking into account the dissociative behaviour of bonding between the radioactive marker and the object as a carrier.

The object underlying the invention thus entirely solved. According to the afore-mentioned first group of inventive methods one determines the mass ($m_2$) having remained on the object after cleaning. Correspondingly, in the second group of inventive methods one determines the mass ($m_1$) being on the object before it undergoes a cleaning action.

In both cases it is possible to obtain an absolute mass value. This value may be determined with any conceivable kind of radiation that makes sense for this particular purpose.

According to a preferred embodiment of the invention, the two groups of methods are combined with each other by determining the ration of the two masses. In such a way it is possible to obtain an exact parameter for the cleaning action. This parameter may be used a basis for the design of the object or for the kind of the cleaning process or for the cleaning agent where one of these two is held constant to optimize the other.

According to another preferred embodiment of the invention, at least one of the intensities ($I_1$, $I_2$) of the radiation of the second mass ($m_1$) or the third mass ($m_2$), respectively, is localizedly measured on the object.

By this measure, known per se, one can detect the cleaning action selectively on particularly critical areas, for example on narrow areas of joints or the like.

For that purpose it is preferred that at least one of the intensities ($I_1$, $I_2$) of the radiation of the second mass ($m_1$) and the third mass ($m_3$), respectively is measured by a camera sensitive for radioactive radiation, in particular for γ-radiation, as also known per se.

It was already mentioned that the inventive method may be used for various applications. A preferred field of application is the field of medical instruments, in particular of hollow shaft instruments for minimum invasive or endoscopic surgery.

Another important medical field of application is the cleaning of flexible endoscopes and the reprocessing of intravasal catheters, in particular coronary catheters. In view of the urgent need within public health care to reduce costs, the validation of processes for reprocessing catheters in lieu of using disposables, will become much more important in the future.

Apart from these applications numerous other applications are possible, for example with respect to parts of food-processing machines or of pharmaceutical installations.

The inventive method and applications preferably relate to situations where the objects to be cleaned shall be cleaned by a machine. However, the invention is not limited to this application, instead, the invention may also be used in cases where the objects are cleaned by hand.

Further, it was already pointed out that the inventive method may also be used for various other purposes, namely for optimizing the design-based cleanability of medical instruments but also for optimizing the design-based cleaning action of washing machines for objects of the kind of interest and also for optimizing the development of cleaning agents.

BRIEF DESCRIPTION OF THE DRAWING

Further advantages can be taken from the description and the accompanying drawing.

It goes without saying that the features enumerated for and those that will be discussed hereinafter may not only be used in the particularly given combination but also in other combinations or alone without leaving the scope of the present invention.

Embodiments of the invention are shown in the drawing and will be discussed in more detail throughout the subsequent description.

FIGS. 1A to 1G show in extremely schematic way various steps of embodiments of inventive methods; and FIG. 2 is a side-elevational view, partly broken away, of a part of an apparatus for carrying out the inventive methods.

In FIG. 1A reference numeral 10 indicates a vessel, for example a glass vessel. The vessel, preferably, has the volume of a common laboratory beaker glass.

In FIG. 1B an arrow 11 indicates that vessel 10 is filled with a soiling substance, in particular a liquid.

In FIG. 1C another arrow 13 indicates that soiling substance 12 is provided with a radioactive marker 14, thus generating a radioactively marked soiling substance 12' has a mass $m_0$. Mass $m_0$ may be measured with appropriate means, for example with a balance or the like (not shown).

The radioactively marked soiling substance 12 is produced, as known per se by, for example, applying radioactive $99^{th}$ technetium to makroalbumines. The radioactive makroalbumines are then mixed with fresh, i.e. coagulable blood. Instead of blood one may also use fibrinogene, for example. In other fields of application outside the field of medical instruments one may use the most persistent dirt as the predetermined soiling substance. For example, if the invention is used in connection with dairy-processing machines, fat may be used. If dish washing machines are used to carrying out the inventive method, egg white may be used, same as in the case where machines for cleaning pharmaceutical installations shall be examined.

As further shown in FIG. 1C, radioactively marked soiling substance 12' is now subjected to a radiation measurement. At this moment in time it is still assumed that the mass of substance 12' is still $m_0$ within an arrow range that is admissible in this case.

For that purpose one may use a Geiger counter 15 measuring the intensity $I_0$ of the initial radiation.

It is important in this respect that concurrently with the execution of the radiation measurement a continuous time measurement is initiated, as indicated in FIG. 1C by a time axis 17. The moment in time at which the initial radiation $I_0$ is measured by means of the Geiger counter 15 is assumed to be $t_0=0$.

As shown in FIG. 1D, a medical instrument 20 is immersed into radioactively marked soiling substance 12', at least with its parts coming into engagement during an operation. Further details will be explained insofar below in connection with FIG. 2.

Instrument 20 having now been contaminated with radioactively marked soiling substance 12' is now subjected to a measurement by means of a γ-camera 25 as shown in FIG. 1B. γ-camera measures the γ-radiation emitted by the technetium. Synchronously with the measurement of the radiation $I_1$ as now prevailing on instrument, the running time is captured and stored at $t_1$. At that moment in time instrument 20 is provided with a mass $m_1$ of radioactively marked soiling substance 12'.

As shown in FIG. 1F, contaminated instrument 20 is now cleaned by a machine as indicated with a washing machine 26 in FIG. 1G.

After the completion of the washing process, the clean instrument 20 is now again measured by means of γ-camera 25. Instrument 20 is now only provided with a mass $m_2$ of radioactively marked soiling substance 12'. The radiation $I_2$ thereof is measured, the corresponding time $t_2$ is captured and stored.

For carrying out the inventive method it is in any case necessary to know the initial mass $m_0$ of the radioactively marked soiling substance 12 as well as the half lifetime T of the radioactive marker.

If, according to a first embodiment of the invention (FIG. 1G), radiation $I_2$ only is measured at $t_2$, the remaining mass $m_2$ of the soiling may be determined according to the following equation:

$$m_2 = \frac{I_2}{I_0} r_{(t,\ldots)} m_0 e^{(t_2/T)\ln 2}$$

where $r_{(t,\ldots)}$ is a predetermined proportionality function for taking into account the dissociative behaviour of bonding between the radioactive marker 14 and the object as a carrier.

If, for example, the marker is attached to the carrier by 100% $r_{(t,\ldots)}$ is a constant, namely unity. If this is not the case, the marker substance as well as the carrier have to be investigated with respect to their concentration as a function of time. Methods for determining this dissociative behaviour are well-known to the skilled person. The corresponding proportionality or correction function $r_{(t, \ldots)}$ results from the special diffusion behaviour with a certain marker substance in relation to a specific carrier, where the function may, inter alia, be time-dependent. Considering that various physical and chemical processes may overlay within this proportionality or correction function and considering, further, that these processes may be partially directed inversely, it may happen that the function is discontinuous because of these individual chemical actions.

If, according to another embodiment of the invention (FIG. 1E), intensity $I_1$ is only measured at $t_1$, one may determine the mass $m_1$ of the soiling on the contaminated instrument 20 prior to the cleaning as follows:

$$m_1 = \frac{I_2}{I_0} r_{(t,\ldots)} m_0 e^{(t_1/T)\ln 2}$$

where $r_{(t, \ldots)}$ is also here the above-discussed proportionality function.

According to a preferred combination of the two afore-mentioned embodiments of the method, one may determine the cleaning action as the ratio of the two afore-mentioned masses $m_2/m_1$.

It goes without saying that γ- camera 25 may alternately measure the entire radiation of instrument 20 or may only measure certain areas of instrument 20 by making localized measurements.

FIG. 2 shows the situation of FIG. 1D in some further detail.

As can easily be seen, vessel 10 is located within a pressure chamber 30. Pressure chamber 30 is closed in a pressure-type manner by means of a cover 31 or lid. An elevated pressure p may be introduced into pressure chamber 30 by applying, for example, compressive air to a connecting pipe 32.

By means of a pressure-tight lead-through 35, the medical instrument 30 is guided through cover 31. For that purpose, an elongate shaft 36 of the instrument 20 extends through lead-through 35 in a pressure-tight manner.

A lower section 37 of instrument 20 is located within the radioactively marked soiling substance 12'. Lower section 37 in particular comprises a forceps 38 or the like attached at the free end of the lower section 37. From the partially broken away view one may see that there are cavities in the interior of elongate shaft 36, for example an annular gap between the wall of elongate shaft 36 and an actuator element for forceps 38 arranged therein, for example a rod, a Bowden pull wire or the like.

The apparatus of FIG. 2 operates as follows:

In order to provide instrument 20 with the radioactively marked soiling substance 12', instrument 20 is pushed with its elongate shaft 36 through lead-through 35. Pressure chamber 30 is then closed in a pressure-tight manner by means of cover 31.

Via connecting pipe 32 an elevated pressure p is fed in. This has the effect that radioactively marked soiling substance 12' is pressed into elongate shaft 36 from below and fills cavity 36 therein up to a predetermined level. The elevated pressure p as well as the duration of the application of pressure p is set such that instrument 20 after the completion of this process is soiled as would be the case during normal operations by assuming a worst case consideration.

What we claim is:

1. A method for determining the cleaning action on a cleaned object, comprising the steps of:

a) providing a predetermined soiling substance;
   b) adding to said soiling substance a radioactive marker having a half life period T, said soiling substance provided with said radioactive marker having together a first mass $m_0$ and a radiation;
   c) measuring said first mass $m_0$;
   d) simultaneously with said measuring of said first mass $m_0$ measuring a first intensity $I_0$ of said radiation and starting a measurement of time t;
   e) at least partially inserting said object into said soiling substance provided with said radioactive marker such that a second mass $m_1$ of said soiling substance provided with said radioactive marker is introduced into at least a portion of said object, thereby, contaminating said object;
   f) cleaning said object;
   g) measuring a third intensity $I_2$ of said radiation at a moment in time $t_2$;
   h) determining a third mass $m_2$ of a soiling having remained on said object after said step of cleaning according to the formula:

$$m_2 = \frac{I_2}{I_0} r_{(t,\ldots)} m_0 e^{(t_2/T)\ln 2}$$

where $r_{(r, \ldots)}$ is a predetermined proportionality function for taking into account the dissociative behaviour of bonding between the radioactive marker and the object as a carrier the third mass m2 being used as an indicator of the cleaning action.

2. The method of claim 1, wherein said radioactive marker is a γ-radiator.

3. The method of claim 1, wherein said object is cleaned by machine.

4. The method of claim 1, wherein said object is a part of a food-treating machine.

5. The method of claim 1, wherein said object is a part of a pharmaceutical installation.

6. The method of claim 1 wherein the ratio m2/m1 is determined.

7. The method of claim 1, wherein said intensity $I_2$ of said radiation of said third mass $m_2$ is localizedly measured on said object.

8. The method of claim 7, wherein said intensity $I_2$ of said radiation said third mass $m_3$ is measured by a camera sensitive for radioactive radiation.

9. The method of claim 1, wherein said object is a medical instrument.

10. The method of claim 9, wherein said medical instrument is a hollow shaft instrument for minimum invasive surgery.

11. A method for optimizing the cleaning action of a washing machine through determining the cleaning action of said washing machine on an object cleaned by said washing machine, the method comprising the steps of:

a) providing a predetermined soiling substance;
   b) adding to said soiling substance a radioactive marker having a half life period T, said soiling substance provided with said radioactive marker having together a first mass $m_0$ and a radiation;
   c) measuring said first mass $m_0$;
   d) simultaneously with said measuring of said first mass $m_0$ measuring a first intensity $I_0$ of said radiation and starting a measurement of time t;
   e) at least partially inserting said object into said soiling substance provided with said radioactive marker such that a second mass $m_1$ of said soiling substance provided with said radioactive marker is introduced into at least a portion of said object, thereby contaminating said object;

f) cleaning said object by said machine;

g) measuring a third intensity $I_2$ of said radiation at a moment in time $t_2$;

h) determining a third mass $m_2$ of a soiling having remained on said object after said step of cleaning by said machine according to the formula:

$$m_2 = \frac{I_2}{I_0} r_{(t,\ldots)} m_0 e^{(t_2/T)\ln 2}$$

where $r_{(t,\ldots)}$ is a predetermined proportionality function for taking into account the dissociative behaviour of bonding between the radioactive marker and the object as a carrier wherein the third mass m2 is used as a means for optimizing the cleaning action of said machine.

12. A method for optimizing the cleaning action of a cleaning agent through determining the cleaning action of said agent on an object cleaned by said agent, the method comprising the steps of:

a) providing a predetermined soiling substance;

b) adding to said soiling substance a radioactive marker having a half life period T, said soiling substance provided with said radioactive marker having together a first mass $m_0$ and a radiation;

c) measuring said first mass $m_0$;

d) simultaneously with said measuring of said first mass $m_0$ measuring a first intensity $I_0$ of said radiation and starting a measurement of time t;

e) at least partially inserting said object into said soiling substance provided with said radioactive marker such that a second mass $m_1$ of said soiling substance provided with said radioactive marker is introduced into at least a portion of said object, thereby contaminating said object;

f) cleaning said object;

g) measuring a third intensity $I_2$ of said radiation at a moment in time $t_2$;

h) determining a third mass $m_2$ of a soiling having remained on said object after said step of cleaning according to the formula:

$$m_2 = \frac{I_2}{I_0} r_{(t,\ldots)} m_0 e^{(t_2/T)\ln 2}$$

where $r_{(t,\ldots)}$ is a predetermined proportionality function for taking into account the dissociative behaviour of bonding between the radioactive marker and the object as a carrier wherein the third mass m2 is used for optimizing the cleaning action of said cleaning agent.

13. A method for validating a cleaning process through determining the cleaning action of said process on an object cleaned by said process, the method comprising the steps of:

a) providing a predetermined soiling substance;

b) adding to said soiling substance a radioactive marker having a half life period T, said soiling substance provided with said radioactive marker having together a first mass $m_0$ and a radiation;

c) measuring said first mass $m_0$;

d) simultaneously with said measuring of said first mass $m_0$ measuring a first intensity $I_0$ of said radiation and starting a measurement of time t;

e) at least partially inserting said object into said soiling substance provided with said radioactive marker such that a second mass $m_1$ of said soiling substance provided with said radioactive marker is introduced into at least a portion of said object, thereby contaminating said object;

f) cleaning said object;

g) measuring a third intensity $I_2$ of said radiation at a moment in time $t_2$;

h) determining a third mass $m_2$ or a soiling having remained on said object after said step of cleaning according to the formula:

$$m_2 = \frac{I_2}{I_0} r_{(t,\ldots)} m_0 e^{(t_2/T)\ln 2}$$

where $r_{(t,\ldots)}$ is a predetermined proportionality function for taking into account the dissociative behaviour of bonding between the radioactive marker and the object as a carrier the third mass m2 is being used for validating the cleaning process.

* * * * *